United States Patent [19]

Kuehnhanss

[11] 4,173,579

[45] Nov. 6, 1979

[54] CONVERSION OF SULFONATED OLEFINS TO SULFONIC ACID SALTS

[75] Inventor: Gerhard O. Kuehnhanss, Baton Rouge, La.

[73] Assignee: Ethyl Corporation, Baton Rouge, La.

[21] Appl. No.: 564,095

[22] Filed: Apr. 1, 1975

Related U.S. Application Data

[63] Continuation of Ser. No. 445,959, Feb. 26, 1974, abandoned.

[51] Int. Cl.$^2$ .................................................. C07C 143/16
[52] U.S. Cl. ................................................... 260/513 T
[58] Field of Search ........................ 260/513 R, 513 T

[56] References Cited

U.S. PATENT DOCUMENTS

| | | | |
|---|---|---|---|
| 3,409,637 | 11/1968 | Eccles et al. | 260/513 T |
| 3,424,693 | 1/1969 | Stein et al. | 260/513 T |
| 3,496,225 | 2/1970 | Logan et al. | 260/513 T |
| 3,579,537 | 5/1971 | Rubinfeld et al. | 260/513 T |

*Primary Examiner*—Nicky Chan
*Attorney, Agent, or Firm*—Donald L. Johnson; John F. Sieberth; Paul H. Leonard

[57] ABSTRACT

Acid mix produced by the sulfonation of olefin with gaseous SO$_3$ is converted to sulfonic acid salts in a two-step conversion wherein the acid mix is partially converted in a first step reaction with anhydrous base providing an anhydrous intermediate product. In a subsequent step, the conversion is carried further by reacting the intermediate product with aqueous base.

15 Claims, No Drawings

CONVERSION OF SULFONATED OLEFINS TO SULFONIC ACID SALTS

CROSS-REFERENCE TO RELATED APPLICATION

This application is a continuation of application Ser. No. 445,959, filed Feb. 26, 1974, in the name of Gerhard O. Kuehnhanss, entitled "Chemical Process", now abandoned.

BACKGROUND OF THE INVENTION

1. Field of the Invention

This invention relates to the preparation of sulfonic acid salts.

2. Description of the Prior Art

The conversion of the product from the sulfonation of olefins into sulfonic acid salts having utility as detergent components is described in numerous patents including U.S. Pat. Nos. 2,061,617; 2,187,244; 3,332,880; 3,488,384; 3,496,225 and 3,642,881. Generally speaking, the conversion has been accomplished in the prior art by reacting the crude sulfonated olefins (acid mix) at elevated temperature with an aqueous solution of a strong base such as NaOH to provide sulfonic acid salts whose cations correspond to those in the base. There is thus obtained a sulfonic acid salt product which may be treated several ways to produce a useful detergent composition. Typically, the amount of water supplied in solution with the base used is adjusted to provide a sulfonic acid salt solution containing 30-40 percent by weight of the salt and which is useful for blending with various detergent active and adjuvant materials such as amine oxides, alkanol amides, alcohol ethoxy sulfates, etc. to produce light duty liquid concentrates useful for dishwashing purposes.

The foregoing conversion of acid mix from olefin sulfonation with base is frequently called hydrolysis or saponification since it usually involves the more or less concurrent conversion of sulfonic acids to salts and the hydrolysis of esters or ester-like materials, including sultones. Generally, the reaction is required to be performed under rather severe conditions with strong reagents (e.g. 150° C. for 1 hour under autogenous pressure using aqueous NaOH) because of the inherent slowness of the hydrolysis of some of the sultone or ester-like materials. Usually a considerable percentage of water is required to be used in the conversion system because aqueous solutions of sulfonic acid salts more concentrated than about 40 percent sulfonic acid salts have a pronounced tendency toward gelling. Such gelling interferes with the conversion as well as with the subsequent use of the product. Unfortunately, the 35-40 percent sulfonic acid salt solutions involve substantial shipping and storage costs because of the water content as well as of the cation material present. This necessitates the existence of numerous small scale sulfonation plants supplying limited geographical areas preventing cost savings that could otherwise be obtained through large scale plant operations. It would be advantageous to have a stable anhydrous composition which can be shipped at lower cost per pound of sulfonate salts or precursors contained therein.

Much of the prior art emphasis in connection with the sulfonation of olefins to produce olefin sulfonate salts is centered about the treatment of $SO_3$ sulfonation effluent acid-mix containing mainly free sulfonic acids and about 30-40 percent sultones. U.S. Pat. No. 3,332,880 describes sulfonate salt mixtures containing about 30-70 percent alkene sulfonic acid salts, about 20-70 percent hydroxy alkyl sulfonic acid salts and about 2-15 percent disulfonate salts. Olefin sulfonation procedures using uncomplexed $SO_3$ are frequently preferred since these procedures are considered to be conducive to the formation of 3- or 4-hydroxy alkane sulfonic acid salts rather than 2-hydroxy alkane sulfonic acid salts.

Olefin sulfonation processes are known to co-produce disulfonates and higher order polysulfonates in appreciable percentages such as 15 percent or higher. Some authorities consider that disulfonates are undesired as detergent components because of their highly polar nature. Usually one can control the production of disulfonates to some extent by controlling the mol ratio of $SO_3$ to olefin used in the sulfonation step. Where the $SO_3$:olefin ratio is about 1:1 or less, the amount of disulfonates is generally less than it is with higher $SO_3$:olefin ratios. On the other hand, $SO_3$:olefin ratios lower than about 1:1 result in poor utilization of the olefins due to the failure of some olefin molecules to be sulfonated. Generally, the prior art prefers an $SO_3$:olefin mol ratio of from about 1:1 to about 1.2:1, typically about 1.1:1 as a reasonable compromise between disulfonates and "free oil" content (unsulfonated olefins).

SUMMARY OF THE INVENTION

There is considerable incentive for improving olefin sulfonation and hydrolysis processing permitting a reduction in shipping costs for the product by providing a stable "high active" concentrate composition of sulfonic acid salt or precursors containing little or no water. The present invention provides a partially converted intermediate product which is substantially anhydrous and which is suitable for placement into containers for shipping or storage. After shipment or storage, the partially converted product is withdrawn from the containers and subjected to further conversion processing, in the course of which water is added forming desired aqueous concentrates of considerable variety of composition such as the 35-40 percent solutions previously mentioned. Residual unsulfonated hydrocarbons in the product preferably are removed by any suitable process, preferably by solvent extraction. Such removal is suitably performed after the partial conversion of the first step or prior to shipping or storing of the partially converted product or it is suitably performed after the aqueous second conversion step.

Various bases are useful in the conversion steps of the process. Alkali metal or ammonium compounds are preferred, especially carbonates, hydroxides and oxides. Some of the suitable compounds are more reactive than others, a fact that is convenient and advantageous for the present process. Sodium methoxide neutralizes sulfonic acids quickly at 0° C. in an anhydrous system. Alkali metal hydroxides react rapidly in the first step even at 10° C. Ammonium carbonate reacts readily in the first step at room temperature. The alkali metal carbonates react readily in the first step at somewhat higher temperatures, e.g. sodium carbonate starts reacting at room temperature and reacts rapidly at about 50° and higher. Substantially more severe conditions are required for the second step conversion than for the first step, the carbonates and bicarbonates react slowly in the second step at temperatures below 150° C. For the second step, hydroxides are preferred, especially sodium hydroxide, with temperatures of from about 100° to about 250° C., in an autoclave or other pressure vessel under autogenous pressure, having present an amount of water which, after the conversion, provides directly the desired solution concentration for the product sulfonic acid salts, typically 35–40 percent by weight. Completion of the second reaction is readily determined by prior art techniques such as those used for determining the progress of a conventional conversion in a one step operation.

Sulfonated olefins used in the present process are preferably obtained by reacting long-chain olefins with uncomplexed $SO_3$ using suitable diluents or heat transfer apparatus or both to control the reaction rate and to remove the heat liberated by the highly exothermic sulfonation reaction. The optional use of various solvents for the olefins as well as the use of nitrogen or other diluents for the $SO_3$ and the use of cooled stirred pot reactors and falling film reactors is known from patents cited herein.

To minimize the formation of color bodies, the sulfonated olefins are preferably treated in the present process promptly, i.e., within from about 0.1 second to about 72 hours after the sulfonation step and bleaching may be employed in accordance with the prior art; however, the present process does not require any critical timing relationship to the sulfonation operation either of the nature of an immediate processing or of aging delay. Some delay is usually inherent as a result of transit time in piping, or of hold-up in supply tanks or heat exchangers and hence is unavoidable.

Thus the present invention is directed to a process for converting into a substantially anhydrous solid product the acid mix produced by the sulfonation of olefins having from about 6 to about 30 carbon atoms per molecule with from about 0.5 to about 2.0 mols of gaseous $SO_3$ per mol of olefin. In this process the crude sulfonated olefins obtained from the sulfonation operation are reacted with substantially anhydrous alkali metal oxide, hydroxide or carbonate or ammonium carbonate to convert only a portion of up to about 90 percent of the sulfonated molecules including at least the free sulfonic acids into sulfonic acid salts thereby forming a mixture consisting essentially of said salts plus at least about 10 percent of the sulfonated molecules in non-salt form.

An important aspect of the present invention is the partial conversion of the product of the sulfonation of olefins into a substantially anhydrous composition of matter which is stable and which is a solid, preferably particulate, that can be handled in bulk storage or in bulk transportation without excessive problems due to deterioration from instability or due to caking, moisture, absorption, etc. which interferes with the removal of the product from bulk containers. A conversion is preferred which converts all free acids to avoid product instability but yet which is partial in terms of the total sulfonated molecules since the product of such a partial conversion has a minimum content of cation material to add weight.

In general, these preferences impose the limitation that the partial conversion converts at least all free sulfonic acids in the sulfonated olefins into sulfonic acid salts but yet does not go so far as to convert all of the sulfonated molecules contained in the product from the olefin sulfonation reaction into sulfonic acid salts, leaving a substantial portion of at least about 10 percent of the sulfonated molecules to be converted to salts in a second conversion step. As is explained in greater detail hereinafter, the crude sulfonation product usually contains some molecules that were not sulfonated. Normally the amount of the unsulfonated molecules is small, less than 10 percent, however, they can be removed readily as for example by solvent extraction. Thus the product from the partial conversion usually contains unsulfonated molecules as well as unconverted sulfonated molecules, the former being readily removed if desired in a subsequent processing step producing a product consisting essentially of sulfonic acid salts and sulfonated molecules substantially free of unsulfonated molecules.

The present invention also relates to a two step conversion process including a partial conversion first step plus a subsequent step wherein the conversion is brought to substantial completion. These two steps are suitably performed in sequence suitably either with or without an intervening separation of unsulfonated molecules.

Thus the present invention is directed to a process for converting into sulfonic acid salts the acid mix produced by the sulfonation of olefins having from about 6 to about 30 carbon atoms per molecule with from about 0.5 to about 2.0 mols of gaseous $SO_3$ per mol of olefin. In this process the crude sulfonated olefins obtained from the sulfonation operation are first reacted with substantially anhydrous alkali metal oxide, hydroxide or carbonate or ammonium carbonate to convert only a portion of the sulfonated molecules including at least the free sulfonic acids into sulfonic acid salts forming an intermediate product. The intermediate product is subsequently reacted in a second conversion step with aqueous ammonium or alkali metal oxide, hydroxide or carbonate to convert additional sulfonated molecules into sulfonic acid salts.

In one aspect, sodium hydroxide is a preferred reactant for both conversion steps of the process. In another aspect, sodium carbonate is used in the first step and sodium hydroxide is used in the second step. Preferably the temperature of the first step is from about 40° to about 150° C., especially from about 75° to about 100° C. Temperatures above about 100° C. generally are not necessary for the first step. Preferably sodium hydroxide is used in the second conversion step at a temperature of from about 120° to about 175° C. Where the temperature of the second step is from about 140° to about 175° C. sodium carbonate is preferred as well as sodium hydroxide.

In one aspect, the sulfonic acid salts produced in the first step are removed from the intermediate product from the first step by solvent extraction prior to the second step conversion of additional sulfonated molecules to sulfonic acid salts. Solvents used for the separation as well as for the removal of neutrals (including unsulfonated molecules) following the second conversion step are preferably hydrocarbon, lower alkanol or lower alkyl ketone. Preferred solvents are polar solvents such as the alkanols and ketones. Preferred lower alkanols are ethanol, propanol, isopropanol and especially methanol. Other suitable solvents are acetone, methyl ethyl ketone, methyl isobutyl ketone and the like.

The amount of base fed at the first step of the conversion process ranges from about the stoichiometric amount required to neutralize the free sulfonic acids present present in the crude sulfonated olefins up to the total amount of base used for both steps of the conversion process. Since it is sometimes desired to use an excess of base of up to about 50 percent above total requirements, the amount of base thus fed at the first step ranges up to about 150 percent of the stoichiometric amount required to neutralize the free sulfonic acids initially present in the crude sulfonated olefins plus those resulting from hydrolysis in both of the conversion steps.

The limit of conversion in the first step can be controlled in several ways. It can be held primarily to neutralization of the free sulfonic acids initially present by feeding only enough base to produce that amount of conversion. When the amount of base feed is in excess of the amount required for neutralization of the free sulfonic acids initially present, the limit of conversion also can be readily limited where desired by selection of the base used and/or by selection of temperatures and reaction times. Thus, for example, hydrolysis in the first step can be limited substantially to hydrolysis of the gamma sultones, e.g., by use of one hour reaction times with sodium carbonate, at a temperature of about 140° C., or e.g. with sodium hydroxide at a temperature of about 100° C. In general, higher temperatures such as 150° C. or higher and with sodium hydroxide are required to hydrolyze delta sultones in reasonable reaction times. Since the conversion of sultones into sulfonic acid salts in the presence of excess anhydrous alkali metal hydroxide produces a high percentage of hydroxy alkyl sulfonic acid salts, one frequently desires to convert the gamma sultones in the first conversion step rather than in the second step, especially where a high percentage of alkene sulfonic acid salts is desired. In such conversion one desires to avoid the use of conditions conductive to the hydrolysis of substantial quantities of the delta sultones in the first step. One readily determines the amount of base required and the temperature and time relationship for the degrees of conversion required at each of the two conversion steps without undue experimentation making it possible to "tailor-make" product sulfonate compositions of a wide variety with a variety of properties.

Preferably the sulfonic acid salts are allowed to remain in the intermediate product although any solvent used is preferably removed. The resulting intermediate product is more or less solid at ordinary temperatures.

In the second step of the process which can be performed after storage or shipping of the intermediate product, water is added, base is added if additional base is required over that fed at the first conversion step and the system is heated to a desired temperature, e.g. 150° C. under autogenous pressure. Conversion of substantially all sulfonated species to sulfonic acid salts thus is obtained. Following the conversion, the product preferably is extracted with a suitable solvent, preferably a hydrocarbon solvent, e.g. pentane or heptane, to remove non-salt materials.

If desired, part or all of the sulfonic acid salts are removed from the intermediate product and the remaining portion of the intermediate product is subjected to the second conversion step separately. The aqueous product resulting from the second step is then extracted to remove non-salt materials and the resulting salts dried to provide anhydrous product if an anhydrous product is desired from the second step. With this type of operation, it is usually preferred to convert at the first step not only the free sulfonic acids but also the gamma sultones. Ordinarily, this is easily accomplished with the typical first stage conditions of NaOH at about 100° C. for 1 to 3 hours, anhydrous in a suitable solvent such as toluene which converts approximately 70 percent of the crude sulfonated olefins into sulfonic acid salts.

Although the presence of water at the first step of the process is undesired, frequently the first step preferably is conducted in the presence of a suitable polar or nonpolar solvent such as a lower alcohol, typically methanol, ethanol or isopropanol or a ketone, typically acetone, methyl ethyl ketone, methyl isobutyl ketone or the like, or hydrocarbons such as alkanes.

Simple alkene sulfonic acid salts and hydroxyl alkyl sulfonic acid salts are not soluble in such solvents whereas the acid mix, sultones, residual olefins, polymers, polyesters etc. are soluble in the solvents.

In the process, the starting mixture of crude sulfonated olefins, base and solvent where used in a dark reddish brown liquid containing the base in suspension. With the agitator running the temperature is adjusted to the desired value. Neutralization of the free sulfonic acids occurs quickly even below room temperature. This is accompanied by a rapid change of color, the system becoming a light yellow mass giving a striking visual indication of reaction. Although the reaction can be carried further than this neutralization of free sulfonic acids state in the first step, even when the agitation is stopped briefly at this point the system usually separates forming a straw-colored waxy layer on top of a relatively clear amber layer. The amber layer will contain the excess base fed over requirements for the first step.

If desired, the top layer is readily separated from the amber solution at this point to provide a sulfonic acid salt mixture which is mostly alkene sulfonic acid, plus about 10 percent disulfonate salts. The amber solution remaining contains solvent when such is used plus sultones and other sulfonated species, plus either residual sulfonic acids or excess base. The solution also contains residual hydrocarbons from the sulfonation operation. Preferably the residual hydrocarbons are separated from the intermediate product whether or not the top layer had been previously removed, and any solvent used is evaporated from the intermediate product leaving a purified intermediate product in more or less solid form. The separation of the residual hydrocarbons from the intermediate product is preferably accomplished by solvent extraction using a suitable solvent such as pentane, hexane and the like. Generally, some of the sultones or other sulfonated molecules will be removed by the solvent; however, this is not a serious problem because, where desired, they can be recycled with the solvent to a point where they build up in the solvent and are not removed by the solvent. Also sultones readily precipitate from solvent systems at temperatures of from about −10° to about 20° C. as limited by the freezing point of the solvent.

The purified intermediate product is a mixture of sulfonic acid salts and non-acidic sulfur containing molecules such as esters and excess neutralizing agent. The material is free of any substantial quantity of water or other diluent and accordingly is an excellent and stable composition for shipment or storage at minimum cost per pound of contained sulfonic acid salt and precursor thereof.

Additional sulfonated molecules contained in the intermediate product are readily converted to sulfonic acid salts in a second conversion step by reacting the intermediate product with aqueous ammonium or alkali metal oxide, hydroxide or carbonate or by reacting it with a salt such as ammonium chloride in accordance with the teachings of U.S. Pat. No. 3,888,918. This step of the process is preferably performed after the intermediate product has been purified, shipped or stored as desired. The compounds to be converted to sulfonic acid salts in this step of the process usually are more difficult to convert than the compounds which react in the first conversion step of the process. Although the weaker bases such as the carbonates usually suffice for the first reacting step, strong bases such as the hydroxides are preferred for the second reacting step together with higher temperatures. The exact temperatures and reaction times for the second conversion step are not particularly critical; however, temperatures above room temperature are preferred, preferably above 100° C., more preferably about 150° C. Temperatures even higher up to about 300° C. may be used; however, generally they are not necessary since convenient reaction times of from about ½ to about 1 hour are generally adequate at 150° C. Below 150° C., the reaction times are generally undesirably long ranging up to 12 hours and more at temperatures of 100° C. and below, particularly when using the carbonates.

A preferred source of starting materials for the present process is an acid mix obtained from the sulfonation of an olefin or an olefin mixture as described in various U.S. Pat. Nos. such as 2,094,451; 2,187,244; 3,332,880 and 3,376,336, said acid mix preferably being taken prior to hydrolysis or other treatment, except possibly bleaching to reduce color. Such an acid mix contains sultones and alkene sulfonic acids as major components along with various other components such as disulfonic acids, unreacted olefins, etc. Free sulfonic acids of various forms present in starting materials are readily converted to their salts in the first step of the present process. Although gamma sultones may be converted to sulfonic acid salts in the first step, preferably the conversion of delta sultones does not occur until the last step. In this way, the first step of the process takes place rapidly at moderate temperature.

Preferred sultones, sulfonic acids and acid mixes useful in the process of the present invention suitably have open or closed or partially closed but preferably open, carbon chain units of from about 6 to about 30 carbon atoms, preferably carbon chain units of from about 10 to about 20 carbon atoms, especially carbon chain units of from about 12 to about 18 carbon atoms. The process is workable with systems which are pure in the sense that all molecules present have the same number of carbon atoms per chain as well as in mixtures containing different carbon chain units. Particularly useful mixtures contain molecules whose uninterrupted carbon chain units contain predominantly the following numbers of carbon atoms: 12 and 14; 12, 14 and 16; 14 and 16; 14, 16 and 18; 16 and 18; 16, 18 and 20; 11, 12, 13, 14 and 15; 12, 13 and 14; 11, 13 and 15; 15, 16, 17 and 18; 15, 17 and 19 and 17, 19 and 21, and the like. These different compositions result in the production of sulfonate salts having desired properties in various water hardnesses, at different temperatures and for cleaning various materials.

The carbon skeleton structures of preferred sultones of sulfonic acids or mixtures or of the components of acid-mixes are saturated or unsaturated, and are straight chain or branched chain, or combinations pure and in mixtures including alkane mono sulfonic acids, alkene mono sulfonic acids, hydroxy alkyl mono sulfonic acids, as well as various disulfonic acids, hydroxy disulfonic acids and the like. Thus mixtures of sultones and/or sulfonic acids converted to sulfonic acid salts can contain entirely straight or branched carbon chain units or other structures or combinations in various proportions. In general, preferred mixtures contain from about 50 to 100 percent of molecules having straight chain carbon skeleton. Preferred sultones are alkyl sultones.

The position of $SO_3$ linkage to the carbon skeleton chains in sulfonic acids of the feed can be at a terminal carbon atom of the chains or at an internal carbon atoms. The positions of $SO_3$ linkage to the carbon chain in sultones or polysulfonated molecules of the feed can be at various combinations of terminal and internal carbon atoms or at internal carbon atoms. Usual mixtures contain various isomers.

A typical acid mix containing sultone, sulfonic acid or both is obtained by sulfonating a mixture of olefins with uncomplexed $SO_3$ in a mol ratio of $SO_3$ to olefin of from about 0.5:1 to about 2:1, said olefins containing 0 to 100 percent vinyl, 0 to 100 percent vinylidene and 0 to 100 percent internal olefins and having from about 6 to about 30 carbon atoms per molecule. Such an acid-mix may be taken from the sulfonation operation and reacted in the present process preferably without intervening treatment with acids or bases. Of course, where desired, various components of such an acid-mix may be selected or rejected using various processes such as solvent extraction and the like.

A mixture of sultones or sulfonic acids or an acid mix containing a mixture in regard to one or more of (1) numbers of carbon atoms per molecule, (2) carbon skeleton structures and (3) position of $SO_3$ linkages to the carbon skeleton structure is generally preferred because such can be readily produced in one operation by sulfonating a mixture of olefins as available in large quantities and at low cost. Preferably such olefin mixtures are selected to produce product sulfonic acid salt having desired properties either per se or when used in combination with various other sulfonate materials generally used in detergent and other surface active formulations.

Typical alkene sulfonic acids processed in accordance with the present invention include: 1-decene-1-sulfonic acid, 2-decene-1-sulfonic acid, 3-decene-1-sulfonic acid, 4-decene-1-sulfonic acid, 1-undecene-1-sulfonic acid, 2-undecene-1-sulfonic acid, 3-undecene-1-sulfonic acid, 4-undecene-1-sulfonic acid, 1-dodecene-1-sulfonic acid, 2-dodecene-1-sulfonic acid, 3-dodecene-1-sulfonic acid, 4-dodecene-1-sulfonic acid, 1-tridecene-1-sulfonic acid, 2-tridecene-1-sulfonic acid, 3-tridecene-1-sulfonic acid, 4-tridecene-1-sulfonic acid, 1-tetradecene-1-sulfonic acid, 2-tetradecene-1-sulfonic acid, 3-tetradecene-1-sulfonic acid, 4-tetradecene-1-sulfonic acid, 1-pentadecene-1-sulfonic acid, 2-pentadecene-1-sulfonic acid, 3-pentadecene-1-sulfonic acid, 4-pentadecene-1-sulfonic acid, 1-hexadecene-1-sulfonic acid, 2-hexadecene-1-sulfonic acid, 3-hexadecene-1-sulfonic acid, 4-hexadecene-1-sulfonic acid, 1-heptadecene-1-sulfonic acid, 2-heptadecene-1-sulfonic acid, 3-heptadecene-1-sulfonic acid, 4-heptadecene-1-sulfonic acid, 1-octadecene-1-sulfonic acid, 2-octadecene-1-sulfonic acid, 3-octadecene-1-sulfonic acid, 4-octadecene-1-sulfonic acid, 1-nonadecene-1-sulfonic acid, 2-nonadecene-1-sulfonic acid, 3-nonadecene-1-sulfonic acid, 4-nonadecene-1-sulfonic acid, 1-eicosene-1-sulfonic acid, 2-eicosene-1-sulfonic acid, 3-eicosene-1-sulfonic acid, 4-eicosene-1-sulfonic acid, 1-heneicosene-1-sulfonic acid, 2-heneicosene-1-sulfonic acid, 3-heneicosene-1-sulfonic acid, 4-heneicosene-1-sulfonic acid, 1-docosene-1-sulfonic acid, 2-docosene-1-sulfonic acid, 3-docosene-1-sulfonic acid, 4-docosene-1-sulfonic acid, 1-tricosene-1-sulfonic acid, 2-tricosene-1-sulfonic acid, 3-tricosene-1-sulfonic acid, 4-tricosene-1-sulfonic acid, 1-tetracosene-1-sulfonic acid, 2-tetracosene-1-sulfonic acid; 3-tetracosene-1-sulfonic acid, and 4-tetracosene-1-sulfonic acid.

Typical hydroxy alkane sulfonic acids processed in accordance with the present invention include 3-hydroxy-decane-1-sulfonic acid, 4-hydroxy-decane-1-sulfonic acid, 5-hydroxy-decane-1-sulfonic acid, 3-hydroxy-undecane-1-sulfonic acid, 4-hydroxy-undecane-1-sulfonic acid, 5-hydroxy-undecane-1-sulfonic acid, 3-hydroxy-dodecane-1-sulfonic acid, 4-hydroxy-dodecane-1-sulfonic acid, 5-hydroxy-dodecane-1-sulfonic acid, 3-hydroxy-tridecane-1-sulfonic acid, 4-hydroxy-tridecane-1-sulfonic acid, 5-hydroxy-tridecane-1-sulfonic acid, 3-hydroxy-tetradecane-1-sulfonic acid, 4-hydroxy-tetradecane-1-sulfonic acid, 5-hydroxy-tetradecane-1-sulfonic acid, 3-hydroxy-pentadecane-1-sulfonic acid, 4-hydroxy-pentadecane-1-sulfonic acid, 5-hydroxy-pentadecane-1-sulfonic acid, 3-hydroxy-hexadecane-1-sulfonic acid, 4-hydroxy-hexadecane-1-sulfonic acid, 5-hydroxy-hexadecane-1-sulfonic acid, 3-hydroxy-heptadecane-1-sulfonic acid, 4-hydroxy-heptadecane-1-sulfonic acid, 5-hydroxy-heptadecane-1-sulfonic acid, 3-hydroxy-nonadecane-1-sulfonic acid, 4-hydroxy-nonadecane-1-sulfonic acid, 5-hydroxy-nonadecane-1-sulfonic acid, 3-hydroxy-eicosane-1-sulfonic acid, 4-hydroxy-eicosane-1-sulfonic acid, 5-hydroxy-eicosane-1-sulfonic acid, 3-hydroxy-heneicosane-1-sulfonic acid, 4-hydroxy-heneicosane-1-sulfonic acid, 5-hydroxy-heneicosane-1-sulfonic acid, 3-hydroxy-docosane-1-sulfonic acid, 4-hydroxy-docosane-1-sulfonic acid, 5-hydroxy-docosane-1-sulfonic acid, 3-hydroxy-tricosane-1-sulfonic acid, 4-hydroxy-tricosane-1-sulfonic acid, 5-hydroxy-tricosane-1-sulfonic acid, 3-hydroxy-tetracosane-1-sulfonic acid, 4-hydroxy-tetracosane-1-sulfonic acid, and 5-hydroxy-tetracosane-1-sulfonic acid.

Typical disulfonic acids and other sulfonic acids processed in accordance with the teachings of the present invention include: 1-decene-1,2-disulfonic acid, 2-dodecene-1,2-disulfonic acid, 2-tetradecene-1,3-disulfonic acid, 5-pentadecene-1,3-disulfonic acid, 3-hydroxy-3-decene-1,2-disulfonic acid, 3-hydroxy-decane-1,5-disulfonic acid, decane-1-sulfonic acid, undecane-1-sulfonic acid, dodecane-1-sulfonic acid, tridecane-1-sulfonic acid, tetradecane-1-sulfonic acid, pentadecane-1-sulfonic acid, hexadecane-1-sulfonic acid, heptadecane-1-sulfonic acid, octadecane-1-sulfonic acid, nonadecane-1-sulfonic acid, eicosane-1-sulfonic acid, tetradecane-2-sulfonic acid, hexadecane-3-sulfonic acid, 2-ethyl-hexadecane-1-sulfonic acid, 2-methyldodecane-1-sulfonic acid. Other sulfonic acids useful are alkyl benzene sulfonic acids having an alkyl chain containing 10 to 18 carbon atoms.

Typical sultones processed in accordance with the present invention include: 3-hydroxydecane-1-sulfonic acid sultone, 4-hydroxydecane-1-sulfonic acid sultone, 3-hydroxy-undecane-1-sulfonic acid sultone, 4-hydroxyundecane-1-sulfonic acid sultone, 3-hydroxydodecane-1-sulfonic acid sultone, 4-hydroxydodecane-1-sulfonic acid sultone, 3-hydroxytridecane-1-sulfonic acid sultone, 4-hydroxytridecane-1-sulfonic acid sultone, 3-hydroxytetradecane-1-sulfonic acid sultone, 4-hydroxytetradecane-1-sulfonic acid sultone, 3-hydroxypentadecane-1-sulfonic acid sultone, 4-hydroxypentadecane-1-sulfonic acid sultone, 3-hydroxyhexadecane-1-sulfonic acid sultone, 4-hydroxyhexadecane-1-sulfonic acid sultone, 3-hydroxyheptadecane-1-sulfonic acid sultone, 4-hydroxyheptadecane-1-sulfonic acid sultone, 3-hydroxyoctadecane-1-sulfonic acid sultone, 4-hydroxyoctadecane-1-sulfonic acid sultone, 3-hydroxynonadecane-1-sulfonic acid sultone, 4-hydroxynonadecane-1-sulfonic acid, 3-hydroxyeicosane-1-sulfonic acid sultone, 4-hydroxyeicosane-1-sulfonic acid sultone, 3-hydroxyheneicosane-1-sulfonic acid sultone, 4-hydroxyheneicosane-1-sulfonic acid sultone, 3-hydroxy-docosane-1-sulfonic acid sultone, 4-hydroxydocosane-1-sulfonic acid sultone, 3-hydroxytricosane-1-sulfonic acid sultone, 4-hydroxytricosane-1-sulfonic acid sultone, 3-hydroxytetracosane-1-sulfonic acid sultone.

Some of the foregoing and additional sultones and sulfonic acids and other materials useful in accordance with the teachings of the present invention are described in terms of a starting material produced by sulfonation of various individual olefins or olefin mixtures exemplified by the following: decene-1, undecene-1, dodecene-1, tridecene-1, tetradecene-1, pentadecene-1, -hexadecene-1, heptadecene-1, octadecene-1, nonadecene-1, eicosene-1, tricosene-1, 2-ethyl-hexene-1, 2-methyl undecene-1, 2-ethyl decene-1, 2-propyl undecene-1, 2-butyl decene-1, 2-pentyl decene-1, 2-hexyl octene-1, decene-2, undecene-3, dodecene-4, tridecene-2, tetradecene-5, pentadecene-7, hexadecene-6, heptadecene-8, octadecene-2, nonadecene-2, eicosene-2, tricosene-2, triacontene-2, 3-ethyl-dodecene-2. Sultone derivatives of the foregoing olefins are generally of the form, 1,2-; 1,3-; 1,4-; 1,5-; 2,3-; 2,4-; 2,5-; 2,6- or the like depending upon the procedures used in sulfonation and on the starting olefin. Alkene sulfonic acids, hydroxy alkyl sulfonic acids and disulfonic acids are isomeric in nature depending to some extent upon the predominant form of the co-present or precursor sultones.

The following examples indicate preferred embodiments and aspects of the present invention.

EXAMPLE I

A sample of crude sulfonated olefin was produced by reacting an olefin mixture containing predominantly tetradecenes and hexadecenes in a 2:1 weight ratio with about 1.1 mol of $SO_3$ per mol of olefin in a falling film reactor at a temperature of about 50° C. The olefins used were as follows:

|  | Weight Percent |
|---|---|
| Dodecenes | 0.3 |
| Tetradecenes | 65.7 |
| Hexadecenes | 34.0 |
|  | 100.0 |
| Average Number of Carbon Atoms per Molecule | 14.6 |
| Average Molecular Weight | 205 |
|  | Mol Percent |
| Vinyl olefins | 80 |
| Vinylidene olefins | 14 |
| Internal olefins | 6 |
|  | 100 |

The olefins were obtained by displacement of the product of chain growth of ethylene or triethyl aluminum.

The crude sulfonated olefins were a thick, reddish brown opaque fluid and had an Acid Number of 113 mg KOH/gram and a Saponification Number of 222 mg KOH/gram.

50 Grams of the crude sulfonated olefins was placed in a 500 ml creased round bottom flask equipped with a thermometer, heater, agitator and a nitrogen sweep system. The contents of the flask were heated to 50° C. and a slow stream of nitrogen turned on. 9.5 Grams of finely ground anhydrous NaOH was then added gradually. This amounts to a 20 percent excess over the amount of NaOH required for complete conversion of all sulfur containing groups to sulfonate salt groups.

The NaOH was added to the flask over a 20 minute period during which time the temperature rose to 70° C. During this time the contents of the flask changed from a dark reddish brown to a bright yellow.

While continuing the stirring, the reaction mixture was cooled to room temperature. The contents of the flask was transferred to a 1-liter stainless steel autoclave and 180 milliliters of water was added. The autoclave was sealed, raised to 150° C. and held at that temperature for 1 hour. The autoclave was then cooled, the contents diluted with 300 milliliters of methyl ethyl ketone, and the clear yellow solution extracted three times with 200 ml portions of a 2:1 volume mixture of methyl ethyl ketone and hexane. The resulting neutral-free solution was fed to a rotating evaporator to remove residual solvents and water. Analysis by thin layer chromatography gave:

|  | Weight Percent |
|---|---|
| Alkene sulfonic acid salts | 64 |
| Hydroxy alkyl sulfonic acid salts | 33 |
| Disulfonic acid salts | 3 |
|  | 100 |

EXAMPLE II

50 Grams of the crude sulfonated olefin described in Example I was dissolved in 100 milliliters of heptane in an open beaker. To the clear brown solution was added slowly and with vigorous stirring 13 grams of finely crushed anhydrous sodium carbonate.

Bubbles of $CO_2$ were noted in the mixture even at room temperature. After 15 minutes had elapsed from the end of the sodium carbonate addition, the temperature had risen to 50° C. and the color of the reaction mixture was light brown. After another 45 minutes had elapsed, the temperature had risen to 70° C. and the color of the mixture was light yellow.

The total reaction mixture was transferred to a 1-liter autoclave, 250 ml water added, the autoclave sealed, heated to 150° C. and held at that temperature for 1 hour.

Solvent and free oil were then removed by extraction, following which the residual solvent and water were removed as in Example I.

The product weighed 56.3 grams and was analyzed by thin layer chromatography giving:

|  | Weight Percent |
|---|---|
| Alkene sulfonic acid salts | 66 |
| Hydroxy alkyl sulfonic acid salts | 29 |
| Disulfonic acid salts | 5 |
|  | 100 |

EXAMPLE III

50 Grams of the crude sulfonated olefin of Example I was dissolved in 100 ml xylene and the brownish but clear solution charged into a 1-liter creased round bottom flask equipped with nitrogen sweep system, mechanical stirrer, with a reflux condenser with distillation receiver which collected the water driven off and returned the xylene to the flask. 50 Grams of sodium carbonate was added to the solution and the flask was placed in an oil bath. The temperature of the flask was raised slowly while stirring and passing a slow stream of nitrogen over the slurry.

15 Minutes later, at a temperature of 43°, the color of the reaction mixture began to change. At slightly under 50°, the slurry had become a light yellow color indicating that the free sulfonic acids had been neutralized.

After about 1 hour, the temperature of the reaction mixture was about 140° and the xylene began to reflux. Water which had formed during the neutralization reaction was then carried out of the flask by the xylene vapor and collected in the distillation receiver, the xylene condensate overflowing the receiver and returning to the flask.

During the first hour at the temperature of the refluxing xylene, 0.08 mol of water collected in the receiver. This is more than theoretical for the neutralization of the free sulfonic acids alone. The reaction mixture was held at xylene reflux for another hour, then the heating was stopped and the slurry allowed to cool to room temperature.

The cold reaction product was dissolved in 400 ml of a 1:1 (volume) mixture of water and methyl ethyl ketone and the excess carbonate neutralized by adding dilute sulfuric acid to bring the solution to a pH of about 8 (22 ml of concentrated $H_2SO_4$ diluted with 50 ml of water was necessary to reach this point).

The neutralized solution was extracted three times with 200 ml portions of a mixture of methyl ethyl ketone and hexane (2:1 ratio by volume), and the aqueous, neutral-free solution evaporated to dryness using a rotating vacuum evaporator. 60.1 Grams of a light beige, dry particulate solid was obtained, a mixture of sulfonate and sodium sulfate.

The inorganic salt was separated from the sulfonate by dissolving the mixture in 750 ml of a 1:1 (volume) mixture of 2-propanol and water and then adding 210 g of $Na_2CO_3$. The aqueous sodium sulfate or carbonate containing phase was discarded, the propanol layer yielding 34.86 g of a light yellow anhydrous, salt-free sulfonate (1).

Removal of the solvents (methyl ethyl ketone and hexane) from the hexane solution left a residue of 14.32 grams which was probably delta sultone and unreacted olefin. This mixture was hydrolyzed by heating it together with a solution of 2 grams NaOH in 38 ml $H_2O$ at 150° for 1 hour.

After cooling, the reaction mixture was diluted with 60 milliliters of methyl ethyl ketone. Non-hydrolyzed material (free oil) was then removed by extraction three times with 100 ml portions of a mixture of methyl ethyl ketone and hexane in 2:1 ratio by volume. 2.18 Grams of free oil was recovered from the hexane layer. 12.85 Grams of anhydrous, oil-free, light colored sulfonate (2) was recovered from the aqueous layer.

Thus from 50 grams of starting crude sulfonated olefin was obtained:

|  |  |  | Weight Percent |
|---|---|---|---|
| Sulfonate 1 | = | 34.86 g | 73.1 |
| Sulfonate 2 | = | 12.85 g | 26.9 |
|  |  |  | 100.0 |

|  | Weight Percent |
|---|---|
| Free oil | 2.18 g |
|  | 49.89 grams accounted for |

The two sulfonates (1) and (2) were analyzed by thin layer chromatography yielding the following in weight percent:

| Component | Alkene Sulfonic Acid Salts | Hydroxy Alkyl Sulfonic Acid Salts | Disulfonic Acid Salts |
|---|---|---|---|
| Sulfonate 1 | 89 | — | 11 |
| Sulfonate 2 | 64 | 34 | — |

Combining sulfonates (1) and (2) therefore provides a product of the composition:

|  | Weight Percent |
|---|---|
| Alkene sulfonic acid salts | 82.3 |
| Hydroxy alkyl sulfonic acid salts | 9.7 |
| Disulfonic acid salts | 8.0 |
|  | 100.0 |

EXAMPLE IV

50 Grams of the crude sulfonated olefins of Example I were reacted with 9.5 grams NaOH (excess for total conversion), anhydrous, without solvent, 50°–75° C. for 16 minutes. In the second step, water was added and the system heated for 1 hour at 150° C. in the autoclave. The product was extracted as in Example I to remove neutrals or free oil and evaporated to dryness. Data are tabulated in Table I.

EXAMPLE V

Example IV was repeated with 100 milliliters of heptane solvent added at step 1. Data are tabulated in Table I.

EXAMPLE VI

Example IV was repeated with 100 milliliters of heptane solvent added at Step I, and with 13 grams of sodium carbonate instead of the sodium hydroxide. Data are tabulated in Table I.

EXAMPLE VII

Example IV was repeated using 200 milliliters of tetradecane as solvent, and 8 grams of sodium carbonate which represents a deficiency of base for complete conversion. Sodium hydroxide (2.3 grams in 190 milliliters of water) was added prior to the second step. Data are tabulated in Table I.

EXAMPLE VIII

Example VII was repeated, however, the crude sulfonated olefins were heated for 1 hour at 100° C. prior to the run. This usually converts gamma sultones into delta sultones. Data are tabulated in Table I.

EXAMPLE IX

In a comparative run, Example IV was repeated with 100 grams of crude sulfonated olefin using a one-step conversion with 21 grams of sodium carbonate, an excess, and 400 milliliters of water at 150° C. for 1 hour. Data are tabulated in Table I.

EXAMPLE X

In a comparative run, Example IV was repeated using a one-step conversion with 9.5 grams of NaOH (an excess) and 180 milliliters of water at 150° C. for 1 hour. Data are tabulated in Table I.

TABLE I

| Example | IV | V | VI | VII | VIII | IX | X |
|---|---|---|---|---|---|---|---|
| First Step - Non-Aqueous System | | | | | | | |
| Solvent | None | $C_7°$ | $C_7°$ | $C_{14}°$ | $C_{14}°$ | No first step | No first step |
| Agent Added | Excess NaOH | Excess NaOH | Excess $Na_2CO_3$ | Deficiency $Na_2CO_3$ | Deficiency $Na_2CO_3$ | | |
| Temp. ° C. | 50–75 | 25–92 | 22–90 | 84–150 | 140° (2 hours) | | |
| Second Step - Aqueous System: 1 HR./150° C. | | | | | | | |
| Agent Added at This Step | None | None | None | NaOH | NaOH | Excess $Na_2CO_3$ | Excess NaOH |
| Recovery Gram/50 g CSO | 54.8 | 54.5 | 56.3 | 52.7 | 51.0 | 67.7 (100 g CSO) | 56.1 |
| Composition by TLC | | | | | | | |
| A= | 64 | 64 | 66 | 67 | 57 | 63 | 57 |
| HA | 33 | 28 | 29 | 23 | 28 | 26 | 32 |
| Di | 3 | 8 | 5 | 10 | 15 | 11 | 11 |
| Klett Color (5 percent Aq. Soln.) | 500 | 660 | 570 | 550 | 730 | 286 | 660 |

EXAMPLE XI

100 Grams of the crude sulfonated olefins of Example I (Acid No.=113 mg KOH/g; Sap. No.=222 mg KOH/g) was dissolved in 100 ml carbon tetrachloride. 10 Grams of ammonium carbonate (5 percent in excess of the theoretical necessary amount for the neutralization of the free sulfonic acids in the CSO) were stirred into the reddish brown solution.

The temperature of the mixture rose from room temperature but was kept below 50° C. by cooling.

After 10 minutes, the color of the slurry had changed to light yellow. Stirring was continued for another 10 minutes at 50° C.

The excess ammonium carbonate was then decomposed by heating the reaction mixture to 60° with stirring. This produced a clear solution which was without sediment.

The light yellow, sediment-free liquid was then cooled to 0°-5° C. At this temperature, all sulfur containing material in the mixture--sultones, etsters, the freshly formed ammonium sulfonates, etc., precipitate out. The precipitate was separated from the solvent by filtering and centrifuging. After removal of residual carbon tetrachloride from the solid phase, 98.6 g of a dry, slightly waxy, storageable and stable product was obtained. The solvent phase from the centrifuge contained about 5 grams of unreacted olefin (free oil). This solvent can be reused preferably after flashing it from the free oil. The product of the preceding step (98.6 g) was heated in an autoclave with an aqueous solution of 17.4 g NaOH in 242.5 ml water under the normal conditions of a hydrolysis in aqueous system (150° C., 0.5 hr.). The resulting solution contained 40 percent actives and was substantially free of neutrals (free oil).

Where it is desired to use the conversion process of Ser. No. 312,948, filed Dec. 1972, to produce alkene sulfonic acid salts and disulfonic acids substantially free of hydroxy alkyl sulfonic acid salts, the purified product (98.6 grams) of the first conversion step is preferably reacted with ammonium or alkali metal halide, such as ammonium chloride at a temperature of from about 125° to about 200° C. The sultones and other sulfonated molecules not converted to salts in the first conversion are then readily converted to salts in this variant of the second conversion.

The data tabulated herein shows Klett color values for the products of various examples. These values are obtained by using a Klett-Summerson Photo Electric Colorimeter with a No. 42 filter (400–465 millimicrons range) and a 4 cm cell length.

The meter is calibrated to zero Klett using deionized or distilled water and the samples are tested in the form of 5 wt. percent aqueous solutions of the sample made up using deionized or distilled water. The lower Klett numbers correspond to materials of lighter color which are generally more desirable at this point. The Klett numbers given are for the products prior to bleaching or desalting operations. In general, the Klett colors obtained after bleaching and desalting were approximately 60 percent of the values given in the Table.

In the Table, the abbreviations A=, HA and Di refer to alkene sulfonic acid salts, hydroxy alkyl sulfonic acid and disulfonic acid salts, respectively.

I claim:

1. A process for converting into sulfonic acid salts the acid mix produced by the sulfonation of olefins having from about 6 to about 30 carbon atoms per molecule with from about 0.5 to about 2.0 mols of $SO_3$ per mol of olefin which comprises:
reacting the sulfonated olefins with substantially anhydrous alkali metal oxide, hydroxide or carbonate or ammonium carbonate to convert only a portion of the sulfonated molecules including at least the free sulfonic acids into sulfonic acid salts thereby forming an intermediate product,
adding water or water plus ammonium or alkali metal oxide, hydroxide or carbonate,
and then reacting the intermediate product to convert additional sulfonated molecules into sulfonic acid salts.

2. The process of claim 1 wherein sodium carbonate is used in the first step and sodium hydroxide is used in the second step.

3. The process of claim 1 wherein the first step is conducted at a temperature of from about 40° to about 150° C.

4. The process of claim 1 wherein the first step is conducted at a temperature of from about 75° to about 100° C.

5. The process of claim 1 wherein the last step is conducted with sodium hydroxide at a temperature of from about 120° to about 175° C.

6. The process of claim 1 wherein the last step is conducted with sodium hydroxide or sodium carbonate at a temperature of from about 140° to about 175° C.

7. The process of claim 1 wherein the sulfonic acid salts produced in the first step are removed from the intermediate product by solvent extraction prior to the second step conversion.

8. The process of claim 7 wherein the solvent used for extraction is hydrocarbon, lower alkanol or lower alkyl ketone.

9. The process of claim 7 wherein the solvent used for extraction is a polar solvent.

10. The process of claim 7 wherein the solvent used for extraction is a lower alkanol.

11. The process of claim 7 wherein the solvent used for extraction is methanol, ethanol, propanol or isopropanol.

12. The process of claim 7 wherein the solvent used for extraction is methanol.

13. The process of claim 1 wherein the amount of base fed at the first step is from about the stoichiometric amount required for neutralization of the free sulfonic acids initially present in the sulfonated olefin up to about 150 percent of the amount required for complete neutralization of the free sulfonic acids initially present plus those resulting from hydrolysis in both conversion steps.

14. The process of claim 1 wherein the amount of base fed at the first step is from about 100 percent to about 150 percent of the stoichiometric amount required to neutralize the free sulfonic acids initially present in the sulfonated olefins plus those resulting from hydrolysis in both of the conversion steps.

15. The process of claim 1 wherein the first conversion step neutralizes the free sulfonic acids initially present in the crude sulfonated olefins, hydrolyses gamma sultones present and neutralizes sulfonic acids produced by hydrolysis of gamma sultones, while avoiding substantial hydrolysis of delta sultones.

* * * * *

UNITED STATES PATENT AND TRADEMARK OFFICE
CERTIFICATE OF CORRECTION

PATENT NO. : 4,173,579
DATED : November 6, 1979
INVENTOR(S) : Gerhard O. Kuehnhanss It is certified that error appears in the above-identified patent and that said Letters Patent are hereby corrected as shown below:

On Cover Page, Item [73] Assignee:

reads "Ethyl Corporation, Baton Rouge, La."
and should read -- Ethyl Corporation, Richmond, Va. --.

Signed and Sealed this

Third Day of June 1980

[SEAL]

Attest:

SIDNEY A. DIAMOND

Attesting Officer

Commissioner of Patents and Trademarks